United States Patent [19]
Winn et al.

[11] Patent Number: 5,092,326
[45] Date of Patent: Mar. 3, 1992

[54] APPARATUS AND METHOD FOR A VENTILATOR SYSTEM

[76] Inventors: Bryan D. Winn, Bryan Winn & Associates, 6812 Alamo Downs Pkwy., San Antonio, Tex. 78238; Howard J. Waugh, Jr., HCR Box 148B, Bigfoot, Tex. 78005

[21] Appl. No.: 122,837

[22] Filed: Nov. 19, 1987

[51] Int. Cl.⁵ ............................................. A62B 9/02
[52] U.S. Cl. ..................... 128/205.13; 128/205.24
[58] Field of Search ............... 128/200.24, 203.12, 128/203.25, 204.18, 204.21, 204.22, 205.11, 205.16, 205.13, 205.18, 205.19, 205.24

[56] References Cited

U.S. PATENT DOCUMENTS

| | | |
|---|---|---|
| 4,001,700 | 1/1977 | Cook et al. |
| 4,036,221 | 7/1977 | Hillsman et al. |
| 4,141,356 | 2/1979 | Smargiassi |
| 4,155,356 | 5/1979 | Venegas |
| 4,210,136 | 7/1980 | Apple |
| 4,215,681 | 8/1980 | Zalkin et al. |
| 4,243,029 | 1/1981 | Apple |
| 4,265,237 | 5/1981 | Schwanbom et al. |
| 4,318,399 | 3/1982 | Berndtsson |
| 4,336,590 | 6/1982 | Jacq et al. |
| 4,340,044 | 7/1982 | Levy et al. |
| 4,351,329 | 9/1982 | Ellestad et al. |
| 4,380,233 | 4/1983 | Caillot |
| 4,401,115 | 8/1983 | Monnier |
| 4,409,977 | 10/1983 | Bisera et al. |
| 4,481,944 | 11/1984 | Bunnell |
| 4,520,812 | 6/1985 | Freitag et al. |
| 4,527,557 | 7/1985 | DeVries et al. |
| 4,587,967 | 5/1986 | Chu et al. |
| 4,589,409 | 5/1986 | Chatburn et al. |
| 4,617,637 | 10/1986 | Chu et al. |
| 4,617,924 | 10/1986 | Heim et al. |
| 4,632,107 | 12/1986 | Butler |
| 4,637,386 | 1/1987 | Baum |
| 4,651,731 | 3/1987 | Vicenzi et al. |
| 4,805,612 | 2/1989 | Jensen ................... 128/205.18 |
| 4,823,787 | 4/1989 | Adahan ................. 128/205.18 |
| 4,838,257 | 6/1989 | Hatch ................... 128/205.24 |

Primary Examiner—Lee S. Cohen
Assistant Examiner—J. P. Lacyk
Attorney, Agent, or Firm—Vinson & Elkins

[57] ABSTRACT

An apparatus and method for a ventilator system which may be operated over a high range of frequencies from zero (0) to fifty (50) hertz as may be predetermined. A high frequency oscillator (14) has a pneumatically operated piston drive device (16) which may be operated at a predetermined frequency, a predetermined stroke length, and at a predetermined ratio between the time periods for the pressure stroke and the suction stroke. The piston (76) is operated from a plurality of solenoid operated valves (91). A microprocessor (92) controls the electronic operation of the valves (91) by suitable output signals.

42 Claims, 4 Drawing Sheets

APPARATUS AND METHOD FOR A VENTILATOR SYSTEM

BACKGROUND OF THE INVENTION

This invention relates to an apparatus and method for a ventilator system and more particularly to such an apparatus and method for a high frequency ventilator system for delivering gas to the airway of a patient.

Heretofore, ventilators have produced gas exchange with the lungs with a frequency generally around the natural frequency of a normal patient's breathing. Such ventilators or ventilator systems have used mixtures of air and oxygen which are humidified and warmed to body temperature and then forced into the lungs under a positive pressure which is adequate treatment for the majority of patients requiring assisted respiration. When patients are exposed to pressure breathing for long time periods however, complications can occur that become life-threatening. Sometimes physiological situations develop that cause the mechanical ventilator to be operated at its maximum limits, and the patient will continue to decline possibly resulting in death. Such situations may occur, for example, from a collapse of the lungs, from the lungs becoming filled with secretions, from airway obstructions, from lungs losing their elasticity, and the like. In these situations, ventilators heretofore have been generally ineffective, particularly in meeting the requirements for such a wide range of complications.

Heretofore, such as shown in U.S. Pat. No. 4,481,944, dated Nov. 13, 1984, a method and apparatus have been provided in a system for applying high frequency positive pressure pulses of gas to an airway of a patient to assist breathing and ventilation. An inhale valve for such gas pulses is opened and closed in response to signals received from a microprocessor. Signals from a temperature sensor and a pressure sensor indicating the temperature and pressure of the gas supplied to the patient are provided to the microprocessor which then supplies appropriate signals to a heater and drive means for controlling the temperature and pressure of the gas supplied to the patient. Additionally, as shown in aforesaid U.S. Pat. No. 4,481,944, the frequency of the gas frequencies, such as from two (2) to thirty (30) hertz or cycles per second. However, the range of frequencies included the natural frequency of the patient's respiratory system at least part of the time and ranged generally between five (5) and ten (10) hertz below the natural frequency, and five (5) to ten (10) hertz above the natural frequency.

Improvements in conventional ventilators have been provided such as illustrated in U.S. Pat. No. 4,036,221, dated July 19, 1977; U.S. Pat. No. 4,527,557, dated July 9, 1985; and U.S. Pat. No. 4,587,967, dated May 13, 1986 which utilize microprocessors receiving input signals from various sensing devices and then sending output signals for controlling the operation of the ventilator. However, such ventilator devices, some of which provide high frequency gas pulses, have not been effective in meeting requirements for a wide range of lung complications encountered as well as assisting normal respiration even though the mechanical breathing action of such ventilators is substantially improved.

Such conventional and high frequency jet ventilators push or force a relatively large volume of air into the lungs in a relatively short period of time, such as one thousand (1,000) cubic centimeters per second and thus, a substantial portion of the air is compressed within the airway or bronchus without reaching the functional areas of the lungs.

SUMMARY OF THE INVENTION

The present invention is directed particularly to an apparatus and method for a ventilator system which may be operated over a wide range of frequencies from zero (0) to fifty (50) hertz or cycles per second (normal respiration less than one hertz) as may be predetermined, or varied continuously by an operator through a keyboard and associated microprocessor. A visual display is continuously displayed for the operator and may show various desired parameters such as the (1) frequency, (2) waveform illustrating pressure of gas delivered to patient in centimeters of water, (3) ratio illustrating the relative periods of the inhalation and exhalation portions of an operating cycle, (4) percentage of oxygen in the delivered gas, (5) temperature of delivered gas, (6) humidity of delivered gas, (7) volume of delivered air in cubic centimeters for each cycle, or in liters per minute, and (8) mean airway pressure (MAP).

The present apparatus utilizes a high frequency oscillator for moving a free flowing column of inspired gas to and from the airway and lungs of a patient at various preselected speeds and waveforms to provide gas flow as may be predetermined for meeting a wide range of lung complications encountered as well as assisting normal respiration. Thus, instead of forcing air into the lungs at relatively high pressures, the present invention utilizes a back and forth flow of air to and from the lungs at relatively low pressures. After the lungs have been initially ventilated, preselected gases may be added to the mixture of gases delivered to a patient, or different concentrations of gases in the gas mixture may be provided, such as varying the concentration of oxygen, for example, or adding anesthesia gas to the inspired gas flow.

A feature of this invention includes means for varying the time period of the pressure stroke in an operating cycle of the apparatus relative to the time period of the suction stroke of the operating cycle. For example, the time period for the positive pressure stroke may be twice the time period for the return suction stroke and this assists in the insertion of selected medication in the gas flow for delivery to the lungs. Likewise, if the time period for the return suction stroke is twice the time period for the positive pressure stroke, the removal of secretions, or other liquids from the lungs is assisted.

It is an object of this invention to provide an apparatus and method for a ventilator system to deliver gas at a predetermined volume and pressure to the airway and lungs of a patient.

An additional object of this invention is to provide a high frequency oscillator for such an apparatus and method for moving a free flowing column of inspired gas to and from the airway and lungs of a patient at various preselected speeds and waveforms to provide a selected gas flow for a wide range of lung complications.

A further object of the invention is to provide apparatus in such a ventilation system in which the time period of the pressure stroke in an operating cycle of the apparatus may be varied relative to the time period of the return suction stroke of the operating cycle thereby to assist in the rapid delivery of desired gases or concentrations of gases to the lungs when the time period of the pressure stroke is greater than the time period of the suction stroke, and to assist in the removal of undesired gases or liquids, such as mucus, from the lungs when the time period of the suction stroke is greater than the time period of the pressure stroke.

Other features and advantages of the invention will become apparent after referring to the following specification and drawings.

BRIEF DESCRIPTION OF THE INVENTION

Figure 1:
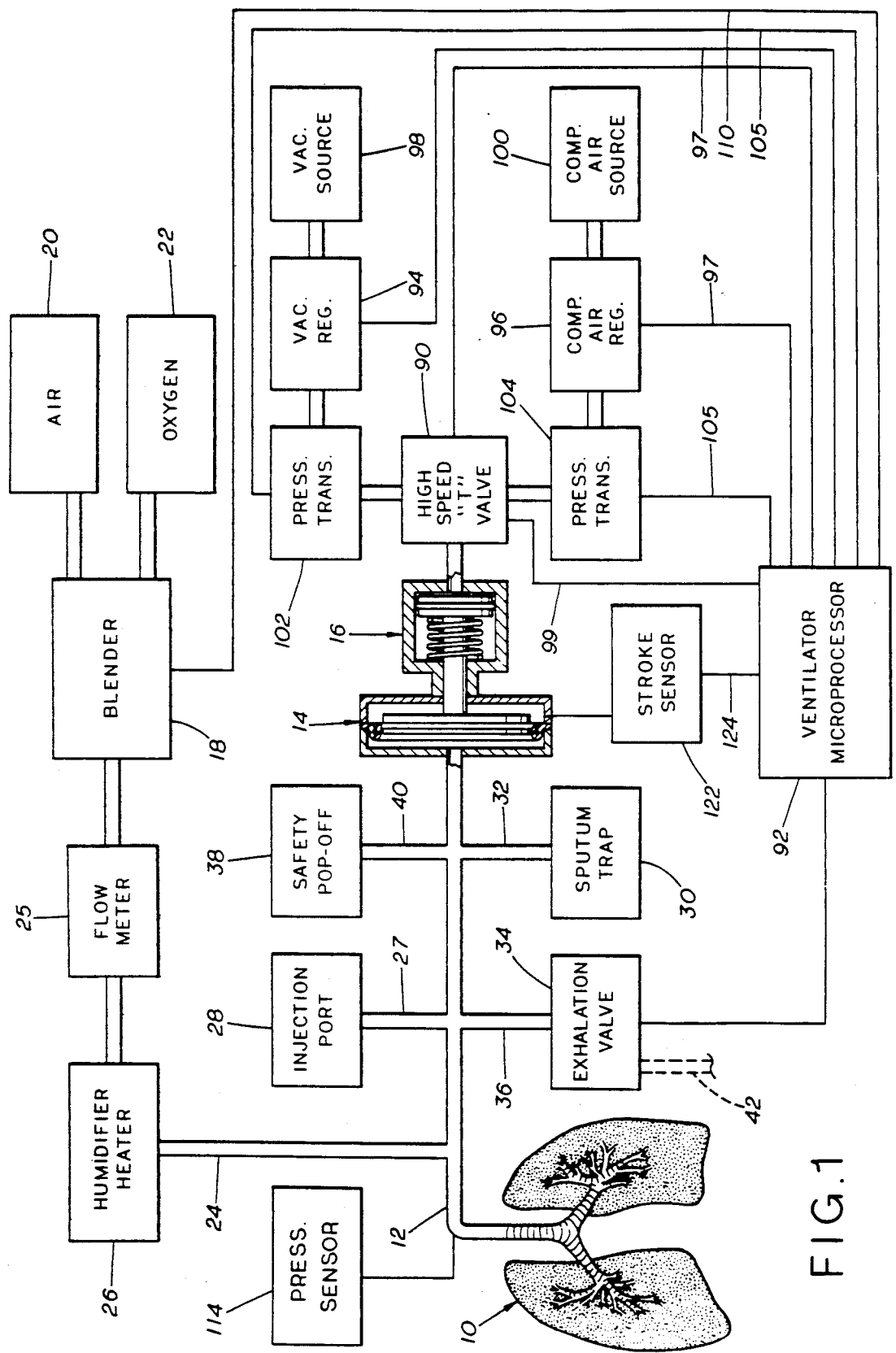
FIG. 1 is a schematic block diagram of the apparatus comprising the present invention for a high frequency ventilator system.

Referring now to the drawings for a better understanding of this invention, reference is made to FIG. 1 in which the lungs of a patient are illustrated schematically at 10. The patient's airway is shown at 12 and a suitable tube or mouthpiece may be inserted within the patient's mouth or nose and throat for the delivery of gas to lungs 10 and the removal of gas from the lungs 10. Airway 12 leads to and is in direct fluid communication with an oscillator indicated generally at 14 which is driven by a piston drive device or means illustrated generally at 16.

To provide a desired or predetermined concentration of oxygen for being inspired or inhaled within airway 12, an oxygen blender 18 connected to an air source 20 and an oxygen source 22 is connected through line 24 to airway 12 to provide the desired concentration of oxygen which may be varied from around twenty-one (21) percent to one hundred (100) percent of the gas inspired within airway 12 and lungs 10. A flow meter 25 and a heater 26 which includes a humidifier are provided for line 24.

To provide desired medication to the patient, a fluid line 27 is connected to airway 12 at one end and its other end is connected to a source of medication 28 for insertion as may be predetermined. To provide a trap or reservoir for the removal of any undesired fluids from lungs 10, a trap indicated at 30 is connected by line 32 to airway 12. An exhalation valve 34 which opens to atmosphere upon exhalation, and is closed upon inhalation is connected by line 36 to airway 12. To maintain the mean air pressure (MAP) within airway 12 below a predetermined maximum in order to prevent possible damage to lungs 10 from abnormally high fluid pressure, a safety valve 38 is connected by fluid line 40 to airway 12 and opens to atmosphere at a predetermined high pressure such as around thirty (30) centimeters of water, for example.

Figure 3:
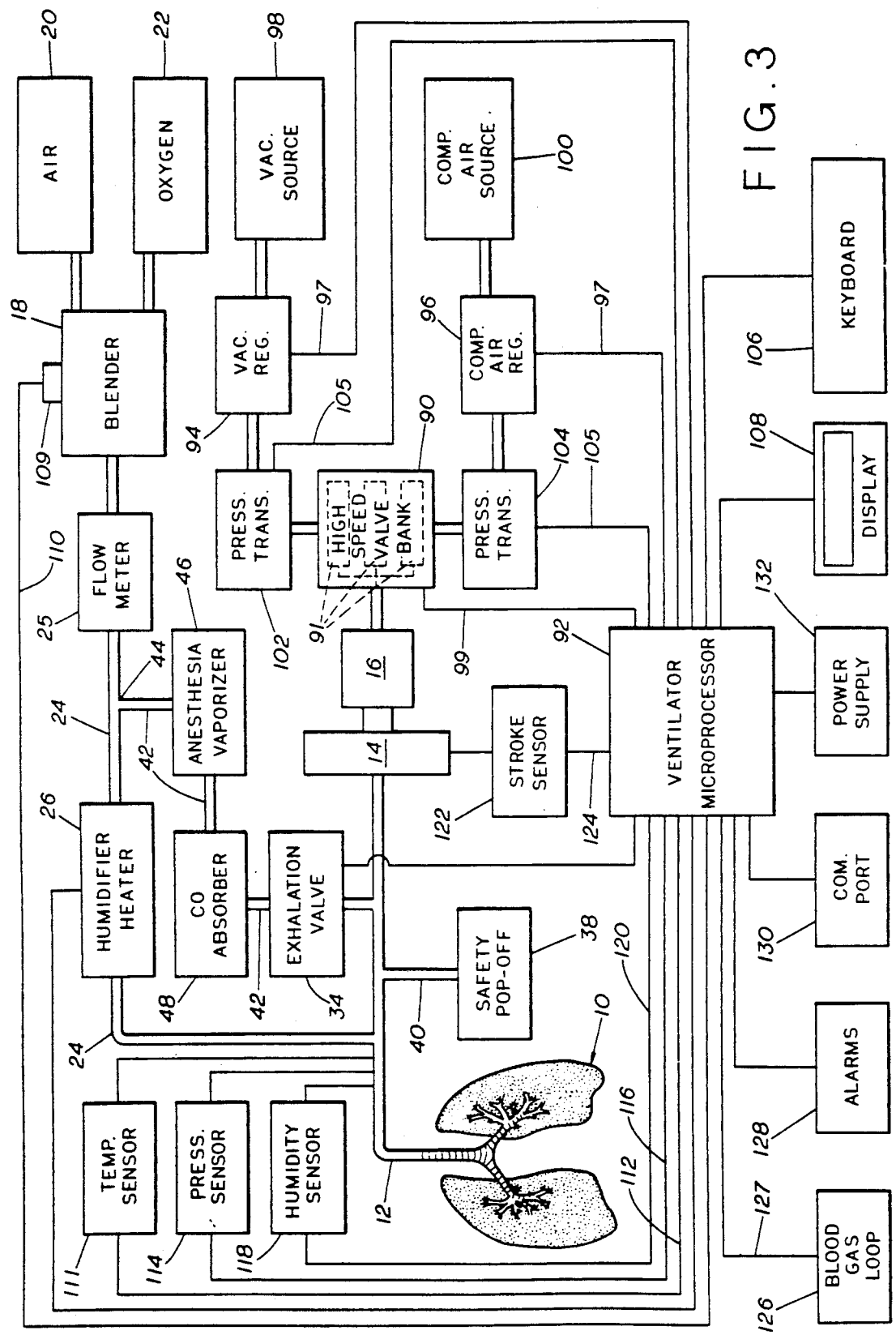
FIG. 3 is a schematic block diagram of the overall system including the microprocessor for receiving and sending signals with associated devices for controlling the operation and functioning of the ventilator.

For delivery of anesthesia, a separate modified breathing line is shown at 42 and is connected to exhalation valve 3 at one end to receive expired gas. The other end of line 42 is connected at 44 to line 24 adjacent flow meter 25 to provide a closed loop. Line 42 as shown in FIG. 3 includes a source of anesthesia gas shown at 46 and a carbon dioxide absorber shown at 48.

Figure 2:
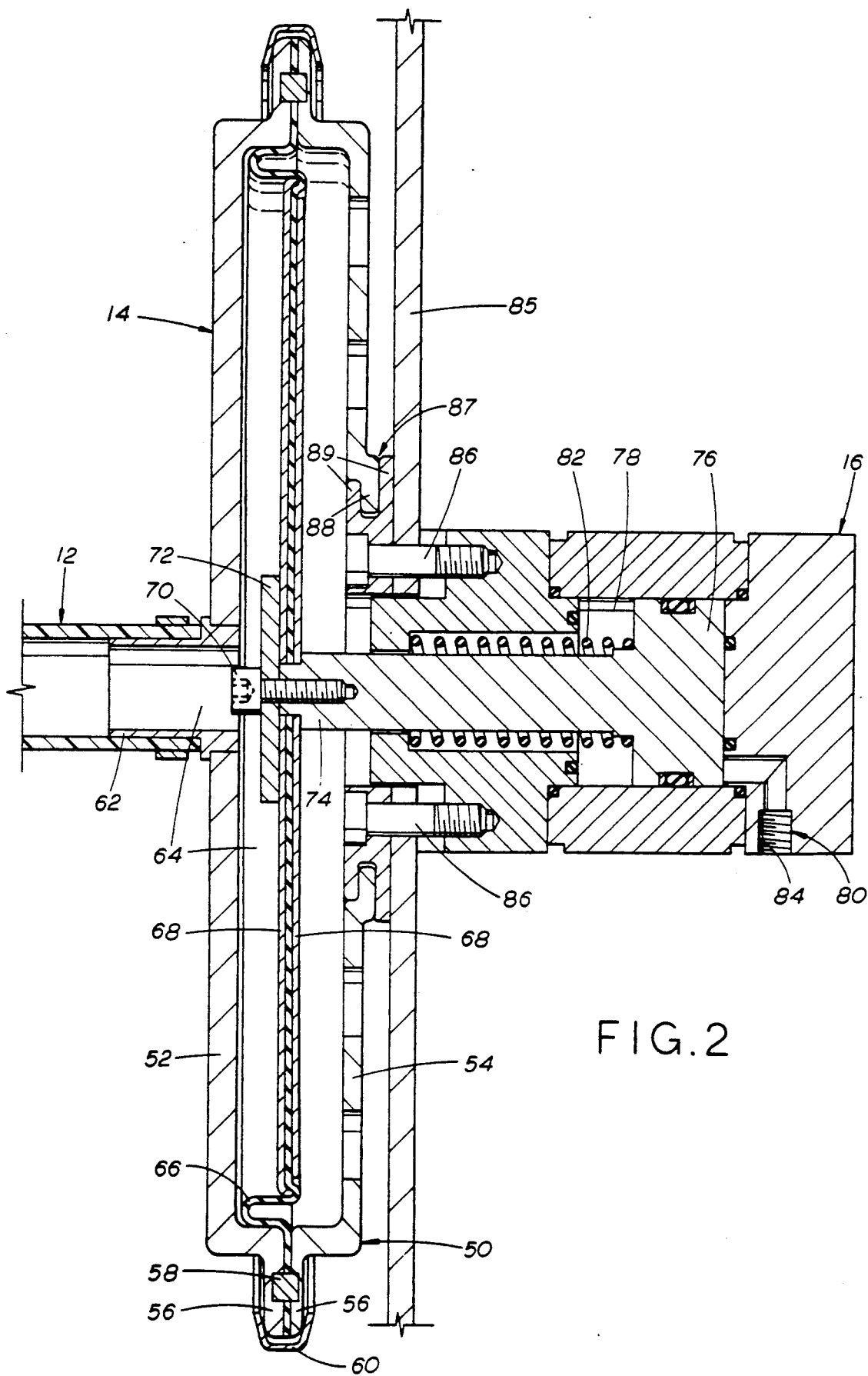
FIG. 2 is a sectional view of the oscillator and associated piston drive member of the apparatus shown in FIG. 1.

Referring now to FIG. 2, oscillator 14 and piston drive device 16 are shown for providing fluid flow to and from the patient at different speeds, amplitudes, and waveforms which includes the pushing and pulling of desired gases or fluids to and from the patient as may be predetermined to provide the maximum amount of gas exchange with the blood in the lungs at the minimum amount of fluid pressure in airway 12. Oscillator 14 comprises a body generally indicated at 50 including a pair of body portions 52 and 54 having matching outer circumferential flanges 56. Dowel pins 58 are provided for the alignment of matching flanges 56 and a removable band 60 is clamped in tight relation about flanges 56. Outer body portion 52 has a connection 62 leading to airway 12 of the patient and defines a fluid chamber 64 in direct fluid communication with airway 12.

Clamped between flanges 56 is a rolling loop flexible diaphragm 66 defining fluid chamber 64 on one side thereof. Diaphragm 66 is clamped between a pair of plates 68 which are secured by a bolt 70 and washer 72 to the end of a piston rod indicated at 74. A pneumatically operated piston 76 is connected to the opposite end of piston rod 74 and is mounted within a piston chamber 78 defined by piston housing or body indicated generally at 80. Spring 82 continuously urges piston 76 to the position shown in FIG. 2. A fluid inlet port 84 leading to fluid chamber 78 through piston housing 80 receives air for driving piston 76 in its power pressure stroke while spring 82 returns piston 76 to its original position upon release of fluid pressure from chamber 78 through port 84.

A fixed base panel or member shown at 85 is provided for mounting piston device 16. A plurality of bolts 86 extend through panel 85 and are threaded within threaded openings in piston housing 80 for securement of piston device 16 to panel 85.

Since flexible diaphragm 66 is exposed to airway 12, it is desirable to remove and replace oscillator 14 when used for another patient. For that purpose, a quick disconnect shown generally at 87 is provided between oscillator 14 and piston drive means 16. A disconnectable clamp 88 fits about flanges 89 and may be easily removed. Then, bolt 70 may be removed to permit the removal of oscillator 14 from the adjacent end of piston rod 74.

Piston device 16 is pneumatically operated in its power stroke and returned by spring 82 in its return suction stroke. The length of the stroke may be adjusted to adjust the displacement of diaphragm 66 and the volume of gas displaced from chamber 64 in an operating cycle for delivery to the patient. Also, the frequency of piston drive means 16 and associated diaphragm 66 may be adjusted for varying the volume and pressure of the air delivered to the patient. Additionally, the time period for the pressure stroke may be adjusted or varied relative to the time period for the suction stroke in an operating cycle as will be explained further hereinafter.

To control the movement of piston 76, a valve bank generally indicated 90 has a plurality of solenoid operated valves 91 preferably three in number but with only one (1) valve 91 being used at any one time. The remaining valves 91 not being used are redundant and utilized only in the event of malfunctioning of the operable valve. A microprocessor 92 controls the electronic operation of valves 91 by output signals sent to valve bank 90 through line 99. A vacuum regulator 94 and a compressed air regulator 96 are connected to valve bank 90. Output signals from microprocessor 92 are sent to regulators 94 and 96 through lines 97. A vacuum source 98 is connected to vacuum regulator 94 and a compressed air source 100 is connected to compressed air regulator 96. Pressure transducers 102 and 104 are connected to the respective regulators 94 and 96 and provide input signals to microprocessor 92 through lines 105 for monitoring the associated fluid pressures.

Figure 4:
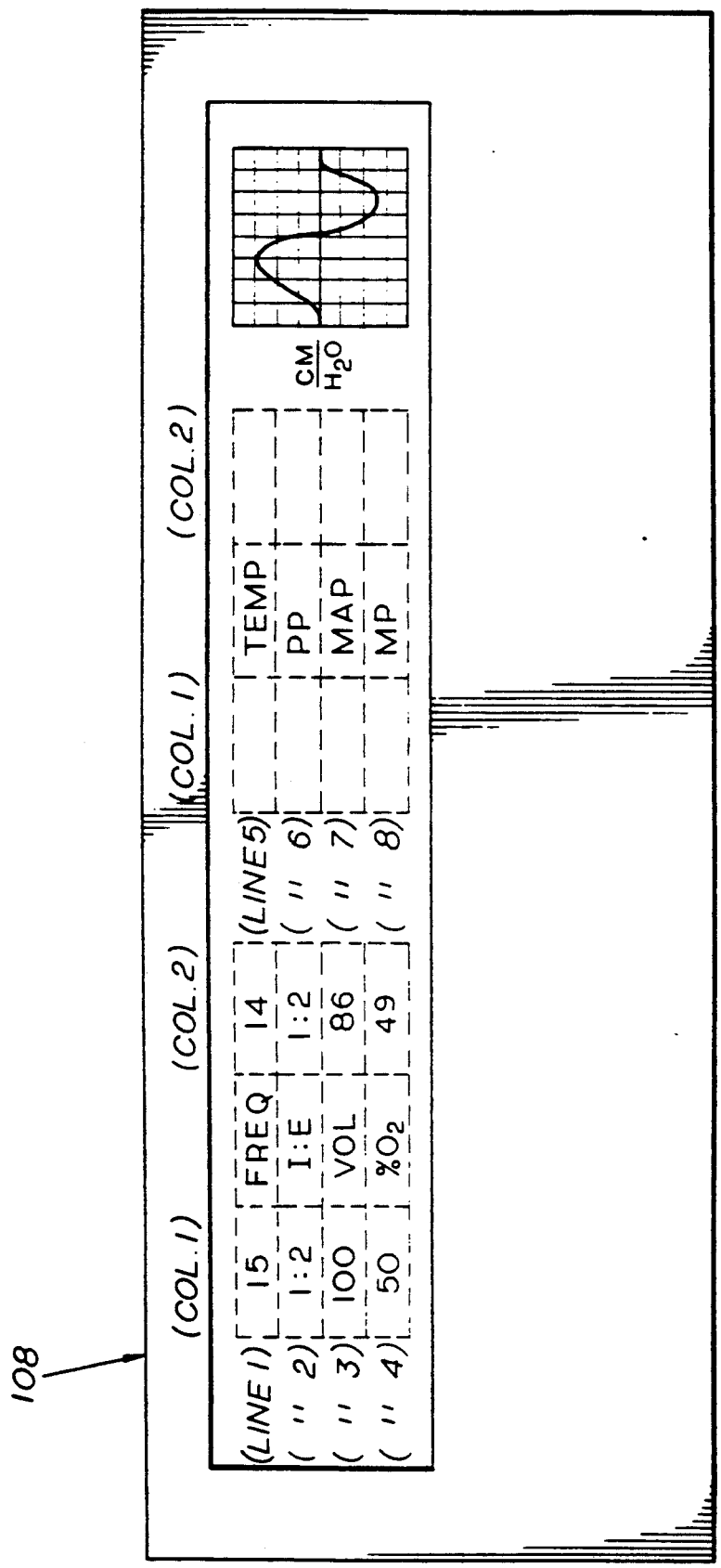
FIG. 4 is a view of the display screen illustrating selected visual information displayed on a screen for observation and use by the operator.

Referring now also to FIGS. 3 and 4 in which the entire ventilator system is shown schematically, keyboard 106 for microprocessor 92 is shown and an operator inserts various desired parameters for controlling the operation of oscillator 14. An operator display is shown at 108 connected to microprocessor 92 and a display screen thereon includes a readout of the desired parameters as selected by an operator. The readout shows in one column the desired or requested parameters and an adjacent column the measured parameters so that an operator may have a visual comparison available at all time. Other sensors in addition to those at pressure transducers 102 and 104 are used for measuring and providing output signals to microprocessor 92 so that suitable or appropriate output signals may be sent by microprocessor 92 to the various control elements. These sensors include sensor 109 for oxygen blender 18 for measuring the percentage or concentration of oxygen in the gas delivered to the patient and sending an input signal through line 110 to microprocessor 92, a temperature sensor 111 connected to airway 12 and providing an input signal through line 112 to microprocessor 92 to provide a measurement of the temperature of the inspired gas, a pressure sensor 114 connected to airway 12 to provide an input signal through line 116 to microprocessor 92 to indicate the mean airway pressure (MAP) of the inspired air delivered to the patient, and a humidity sensor 118 connected to airway 12 to provide a measurement of the moisture in the gas delivered to the patient and an input signal through line 120 to microprocessor 92. A stroke sensor shown at 122 measures the frequency of oscillator 16, the length of stroke, and the time period of the pressure stroke of oscillator 14 relative to the time period of the return suction stroke of oscillator 14. Output signals from sensor 122 are provided through line 124 to microprocessor 92 from stroke sensor 122. The output signals from sensor 122 will be analyzed by the microprocessor 92 to determine the volume of air being displaced as well as the actual frequency and I:E ratio. These measurements will be compared to the preselected settings to verify the proper operation of the patient oscillator 14.

A blood gas loop shown at 126 provides an input signal through line 127 to microprocessor 92 concerning blood ga values which may be entered manually or through a computer of the associated installation, such as a hospital, at which the system is located so that the system maintains blood gas values within a certain predetermined range controlled by microprocessor 92. Normally, blood from the patient is analyzed continuously by a hospital to determined the levels of oxygen and carbon dioxide in the blood in addition to the blood pressure. This information is utilized by microprocessor 92 from an input signal from blood gas loop 26.

Audible alarms are shown at 128 and such alarms may be provided for any of the desired parameters which may be outside a predetermined range. This would include alarms, for example, activated when a pressure is reached outside the range for pressure transducers 102 and 104, or outside the range for the airway pressure measured by sensor 114, or upon a failure of any of the solenoid operated valves 91 in valve bank 90. The conditions under which alarm 128 is activated may be displayed on display 108, if desired.

A communications port shown at 130 is provided for external monitoring and control such as at a remote location. Such an interface may comprise an IEEE (Institute of Electrical and Electronic Engineers) type 488 port.

To provide power for the microprocessor 92, the regulators 94 and 96, the high speed valve bank 90, the transducers 102 and 104, and the various sensors, a power supply is indicated at 132 which will convert standard AC voltage obtained from the installation at which the system is housed and convert it to the required DC voltage.

In operation, oscillator 14 is communicated with airway 12 and lungs 10 of a patient. Certain requirements or desired parameters for the patient have been predetermined and this information is fed by an operator on keyboard 106 to microprocessor 92 and displayed on operator display 108. As illustrated in FIG. 4, in which a typical display screen is shown two parallel columns are shown side by side for quick comparison, with column 1 illustrating the desired parameters as inserted from keyboard 106 and the other column 2 indicating the parameter as measured by the various sensors. For example, column 1 of line 1 represents a desired frequency of fifteen (15) hertz or cycles per second and column 2 of line 1 represents a measured frequency from sensor 122 shown as fourteen (14) hertz. Line 2 illustrates the ratio between the time periods for the inspiration and the expiration strokes of an operating cycle for oscillator 14. Both the desired ratio in column 1 and the measured ratio in column 2 measured by sensor 122 indicate the time period for the expiration stroke is twice the time period for the inspiration stroke. Sensor 122 provides an output signal through line 124 to microprocessor 92 to confirm the desired ratio. The desired volume of the inspired gas is shown in column 1, line 3 as one hundred (100) cubic centimeters for each cycle, and the measured volume is eighty-six (86) cubic centimeters as sensed by sensor 122. The desired oxygen concentration in line 4 is fifty (50) percent and the measured oxygen concentration is forty-nine (49) percent as measured by sensor 109 at blender 18.

The mean airway pressure (MAP) is sensed by pressure sensor 114 and the temperature is sensed by sensor 110 with output signals to microprocessor 92. The peak pressure (PP) is shown in line 6 and the minimum pressure (MP) is shown in line 8 with such pressures being measured by sensor 114. Such peak and minimum pressures over a fixed time period are provided.

The waveform illustrating mean airway pressure in centimeters of water is shown on the display screen as illustrated in FIG. 4 and the minimum or maximum values of the mean airway pressure is visually monitored at all times from the screen on display 108.

The volume of the gas delivered to the patient is computed by microprocessor 92 based on the output signals from stroke sensor 122 and in the event it is desired to change such volume, microprocessor 92 sends an output signal to regulators 94 and 96. Valve bank 90 responds to a signal from the microprocessor 92 and increases or decreases the frequency until sensor 122 signals to microprocessor 92 that the frequency is in accordance with the input from keyboard 106. The compressed air and vacuum regulators 94 and 96 respond to signals from microprocessor 92 which increases or decreases the length of the stroke. Signals from sensor 122 input to microprocessor 92 are used to verify the required stroke length and associated volume as specified by the input from keyboard 106. Keyboard 106 likewise determines the required waveform along with the frequency, length of stroke, airway pressure limits, temperature, percent of oxygen in the inspired gas, and any alarm limits. Microprocessor 92 compares the input from keyboard 106 with stored information. Measurements from oxygen sensor 109, temperature sensor 111, pressure sensor 114 for the fluid pressure in airway 12, length of stroke and frequency of oscillator 14 from sensor 124, air pressure for piston drive means 16 as measured at pressure transducers 102 and 104, humidity sensor 118 for the humidity of the gas in airway 12, all provide output signals to microprocessor 92 for comparison with the information fed to the microprocessor 92 from keyboard 106. All of the parameters requested by operator 106 will be displayed on column 1 of display 108 and the measured parameters will be displaced on column 2 for comparison. The display readout on FIG. 4 and the waveform display thereon provide for a safe operation of the system.

The present invention is particularly adapted for operating within a wide range of parameters including the ventilation of premature babies weighing one (1) or two (2) pounds as well as animals having a weight of fifteen hundred (1,500) pounds or more. Oscillator 14 may be sized for a specific displacement and it is envisioned that three (3) sizes of oscillator 14 should meet all requirements. The volume of gas displaced and delivered to airway 12 and lungs 10 range from zero (0) cubic centimeters to fifteen hundred (1,500) cubic centimeters as may be predetermined.

A suitable heater and humidifier 26 may be of the cascade type manufactured by Puritan-Bennett Inc., Oak & 13th Street, Kansas City, Mo. Flow meter 25 may be of the floating ball type having a capacity of 0-15 LPM (liters per minute) manufactured by Puritan-Bennett, Inc. Oak & 13th Street, Kansas City, Mo.

It is apparent from the foregoing that various combinations or ranges of selected parameters may be provided by the present apparatus and method. For example, oscillator 14 may operate at a frequency between zero (0) hertz and fifty (50) hertz and the volume displacement of oscillator 14 may be between zero (0) cubic centimeters per cycle to fifteen hundred (1,500) cubic centimeters per cycle. It is noted that the time period of the pressure stroke of oscillator 14 may be varied as desired in relation to the time period of the suction stroke of oscillator 14 for an operating cycle. For example, the time period for the positive pressure stroke may be twice the time period for the return suction stroke thereby to assist in the insertion of selected fluid or medication agents in the airway 12 for delivery to lungs 10. Also, if the time period for the return suction stroke of oscillator 14 is twice the time period for the positive pressure stroke, the removal of secretions, and other liquids from the lungs 10 through airway 12 for disposal in trap 30 is assisted. Thus, oscillator 14 moves a column of gas within airway 12 back and forth in response to the movement of oscillator 14 under minimum airway pressures. The time period for the pressure and suction strokes are controlled by a plurality of solenoid operated valves in valve bank 90, and associated regulators 94, 96 which receive signals from microprocessor 92 to vary the periods between the pressure stroke and suction stroke of oscillator 14. Such a variety of options provided by the present system permit the present method to meet the requirements for a wide range of lung complications encountered as well as assisting normal respiration.

As an example of the operating use of the present invention, the following operating procedures may be utilized. First the desired parameters as illustrated on display 108 are selected and provided by an operator from keyboard 106 to microprocessor 92 and display 108. These parameters will include the desired oxygen content in the gas delivered to the patient, the volume of gas delivered to the patient, and the mean airway pressure for the patient. From the desired volume and desired pressure, oscillator 14 will be provided with an initial frequency, length of stroke, and ratio between the time periods for the pressure and suction strokes for an operating cycle. Then, oscillator 14 is connected to the patient and breathing gas provided with an oxygen content of twenty-one (21) to one hundred (100) percent is bled into airway 12 from blender 18 at approximately five (5) to ten (10) liters per minute. The exhalation valve 34 is set to retard exhaust flow until the lungs open and inflate. This creates a positive pressure inside the lungs of about fifteen (15) to twenty (20) centimeters of water ($cmH_2O$). After valve 34 is set, air bleeds from exhaust valve 34 at the same flow rate it enters airway 12 and air flow equilibrium is established.

Next, the oscillating frequency of oscillator 14 is set at a frequency between five (5) to fifteen (15) hertz. The waveform control is normally set so that the time period of the suction stroke is twice the time period of the pressure stroke to provide a one (1) to two (2) ratio. The total time of the forward and return strokes will vary according to the frequency setting.

The next control setting is the length of stroke or amplitude control which is usually set at about thirty (30) percent of full travel which may be around one-sixth (1/6) half inch for example.

The operation of piston drive mean 16 and associated oscillator 14 is then commenced The airway pressure is continuously monitored for maintaining a positive pressure at about fifteen (15) to twenty (20) cm $H_2O$. It may be necessary to adjust either the volume of the air flow or the exhaust opening of exhalation valve 34 to maintain a specific desired pressure After around five (5) minutes of operation, an arterial blood ga sample is taken from the patient by other apparatus to determine the amount of oxygen and carbon dioxide in the blood and the pressure ranges thereof. Normal pressure ranges of such blood gases are from eighty (80) to one hundred and five (105) millimeters of mercury (mm Hg) pressure for oxygen, and from thirty five (35) to forty five (45) mm Hg for carbon dioxide at a pH between 7.35 and 7.45.

A patient in acute respiratory failure would have an oxygen pressure level of less than sixty (60) mm Hg, and a carbon dioxide pressure level of more than sixty (60) mm Hg at a pH less than 7.35. If such a patient is utilizing a conventional ventilator set at one hundred (100) percent oxygen, a respiration rate of ninety (90) breaths per minute, a volume of one thousand (1,000) cc per breath, and a pressure of ninety (90) cm $H_2O$; and the patient had an oxygen pressure level of forty (40) mm Hg, and a carbon dioxide pressure level of eighty (80) to one hundred (100) mm Hg with a pH of 7.29; then the patient would be in severe respiratory failure. If the patient is then placed on the high frequency ventilator system shown in FIG. 3 at this point, after five (5) minutes the arterial blood sample could typically have an oxygen pressure level of around two hundred twenty (220) mm Hg, a carbon dioxide pressure level of forty (40) mm Hg and a pH of 7.45. In this event, the oxygen pressure is too high and can be reduced by lowering the oxygen concentration from fifty (50) percent to thirty (30) percent and another sample taken in five (5) minutes. The oxygen pressure is usually maintained at one hundred (100) to one hundred fifty (150) mm Hg at the lowest possible oxygen concentration and airway pressure.

If the oxygen concentration was at one hundred (100) percent and the blood gas oxygen level was too low, then increasing the airway pressure from fifteen (15) to twenty (20) cm $H_2O$ to as high as ninety (90) cm $H_2O$ will increase the lung capacity or surface area exposed to ventilation and thereby increase the arterial oxygen level. However, it is usually desirable to use the lowest possible pressure and oxygen concentrations at all times. If the carbon dioxide pressure remains greater than forty-five (45) mm Hg, it could be reduced by increasing the oscillator volume and selecting a new frequency by trial and error. However, it is desirable to have a minimum airway volume at a minimum frequency for oscillator 14.

If the carbon dioxide pressure is normal, e.g. thirty-five (35) mm Hg, the blood pH will generally fluctuate to its normal range of 7.35 to 7.45. If the normal pH range is not reached within a reasonable time, chemical injections of sodium bicarbonate may be employed for obtaining the deemed pH level.

During ventilation, secretions in the lungs must be removed so that respiration is not obstructed. To accomplish this, the ratio between the time periods of the pressure stroke and suction stroke is adjusted. With any equal time period, particulate matter in the airways will remain because it is being pushed and pulled for the same amount of time in each direction. If the waveform control is set so that the pressure stroke is less than fifty (50) percent of the total stroke time, then particles are pushed into the lungs for a shorter period than they are pulled out so they begin to move out. The reverse is true if the control is set so that the pressure stroke is greater than fifty (50) percent of the total stroke time. Particles are then pushed in longer than they are pulled out so they move into the lungs. Inward movement may be used to deposit medication and outward movement to cleanse the lungs. This movement ability has sublateral therapeutic benefits since clean lungs become normal healthy lungs.

The present invention may be used to ventilate emergency victims suffering from suffocation, drowning, foreign gas inhalation, automobile, or other accidents. Also, certain patients may utilize the present invention at home for the treatment of chronic obstructive lung diseases such as asthma, bronchitis, and emphysema where the patient is suffering from inability to loosen and remove secretions from his airways and lungs.

While preferred embodiments of the present invention have been illustrated in detail, it is apparent that modifications and adaptations of the preferred embodiments will occur to those skilled in the art. However, it is to be expressly understood that such modifications and adaptations are within the spirit and scope of the present invention as set forth in the following claims.

What is claimed is:

1. A system for controlling the inhalation and exhalation of a gas mixture to and from an airway of a patient comprising a gas chamber and a gas delivery line extending from the gas chamber to the airway of the patient;

an oscillating member supported in said gas chamber for movement in a pressure stroke in one direction for providing gas to the airway and a suction stroke in an opposite direction for exerting a suction to aid in exhalation of gas from the airway;

a piston and cylinder combination connected to said oscillating member for moving said oscillating member at a desired frequency and length of stroke, said combination including a piston chamber and piston mounted therein for reciprocal movement;

pneumatically operated means operatively connected to said combination for selectively providing air to said piston chamber for driving said piston; and a microprocessor operatively connected to said pneumatically operated means for controlling the frequency and length of stroke of said piston.

2. A system as set forth in claim 1 wherein said pneumatically operated means includes a solenoid operated pneumatic valve connected to said piston and cylinder combination and a source of compressed air for said pneumatic valve, and said microprocessor provides an output signal for actuation of said pneumatic valve.

3. A system as set forth in claim 2 wherein a regulator is provided between said source of compressed air and said pneumatic valve, and said microprocessor provides an output signal to said regulator for controlling the actuation of said pneumatic valve.

4. A system as set forth in claim 2 wherein said solenoid operated pneumatic valve includes a plurality of redundant solenoid operated pneumatic valves operatively connected to said piston and cylinder combination and being operative only in the event of malfunctioning of the pneumatically operated pneumatic valve.

5. A system as set forth in claim 1 wherein said pneumatically operated means includes a solenoid operated pneumatic valve connected to said piston and cylinder combination;

a source of compressed air for said pneumatic valve utilized in the pressure stroke of the oscillating member;

a vacuum source for said pneumatic valve utilized in the suction stroke of the oscillating member;

a regulator between said source of compressed air and said pneumatic valve;

a regulator between said vacuum source and said pneumatic valve; and said microprocessor providing output signals to said regulator for controlling the actuation of said pneumatic valve and said oscillating member.

6. A system as set forth in claim 5 wherein a pressure transducer is provided for each regulator for sensing the fluid pressure thereat, and an output signal is sent by each pressure transducer to said microprocessor representing the positive fluid pressure and negative fluid pressure exerted against said pneumatic valve.

7. A system as set forth in claim 1 wherein said oscillating member comprises a diaphragm mounted within said gas chamber and exposed to the airway of the patient; and said oscillating member including a quick disconnect mechanism for removal and replacement.

8. A system as set forth in claim 1 wherein an oxygen source is in fluid communication with the gas delivery line to said airway, and said microprocessor controls the amount of oxygen supplied to the airway from the oxygen source.

9. A system as set forth in claim 1 wherein a source of air and a source of oxygen are in fluid communication with the gas delivery line to said airway, and said microprocessor controls the gas mixture of oxygen and air supplied to the airway.

10. A system as set forth in claim 9 wherein means are provided to moisten said gas mixture supplied to the airway, and said microprocessor controls the amount of moisture supplied to the gas mixture.

11. A system as set forth in claim 9 wherein means are provided to heat said gas mixture supplied to said airway to a predetermined temperature, and said microprocessor controls the predetermined temperature to which said gas mixture is heated.

12. A system as set forth in claim 1 wherein means are provided to vary the time period of the pressure stroke in an operating cycle in relation to the time period for the suction stroke in an operating cycle.

13. A system as set forth in claim 12 wherein the time period for the pressure stroke in an operating cycle is substantially greater than the time period of said suction stroke thereby to assist in the rapid delivery of a predetermined medication to said airway.

14. A system as set forth in claim 12 wherein the time period for the suction stroke of an operating cycle is substantially greater than the time period for said pressure stroke thereby to assist in a rapid removal of fluids from the airway.

15. A system as set forth in claim 1 wherein an anesthesia gas source is provided in fluid communication with said air delivery line to the airway for delivery to the patient.

16. A respiratory system for controlling the delivery of gas to the airway of a patient comprising:
   a displacable gas delivery means for forcing periodically in one direction of travel a volume of gas under pressure into the airway of a patient throughout an inhalation period of a respiratory cycle for effecting flow of said gas to the airway;
   drive means operatively connected to said gas delivery means to displace the volume of gas to be delivered in a positive pressure stroke in one direction of travel from a first position to a second position and to effect the flow of gas from the airway throughout an exhalation period of the respiratory cycle in a return suction stroke in an opposite direction of travel from the second position to the first position; and
   means to vary the frequency of the respiratory cycles to a predetermined number of cycles per second; and
   means are provided to vary the time period of the inhalation period of the respiratory cycle relative to the time period of the exhalation period thereof; and
   said drive means comprises a piston and cylinder combination and said displacable gas delivery means comprises a diaphragm operatively connected to the piston for movement therewith.

17. The respiratory system of claim 16 wherein a source of air and a source of oxygen are in fluid communication with the gas delivery means for providing a predetermined mixture of air and oxygen to the patient.

18. The respiratory system of claim 16 wherein a microprocessor is operatively connected to said drive means for controlling the operation of said drive means; and
   means are provided to sense the fluid pressure in said airway and to provide an output signal to said microprocessor representing said airway fluid pressure.

19. The respiratory system of claim 16 wherein a microprocessor is operatively connected to said drive means for controlling the operation of said drive means; and
   an operator keyboard and associated display are operatively connected to said microprocessor for providing a predetermined frequency for said gas delivery means.

20. The respiratory system of claim 16 wherein a source of air and a source of oxygen are in fluid communication with the gas delivery means; and
   means are provided to sense the amount of oxygen in said gas and to provide an output signal to said microprocessor for indicating the oxygen concentration.

21. Apparatus for controlling inhalation and exhalation of gas to and from the lungs of a patient comprising:
   gas delivery means for delivering gas to an airway of a patient in a pressure stroke and assisting in the removal of gas from the airway in a suction stroke, said gas delivery means including a pneumatically operated piston having a diaphragm mounted on one end thereof for reciprocation with said piston;
   a solenoid operated pneumatic valve operatively connected to said piston;
   a source of compressed air for said pneumatic valve;
   a regulator between said source of compressed air and said pneumatic valve; and
   a microprocessor for controlling and providing an output signal to said regulator for controlling the actuation of said pneumatic valve and associated piston.

22. Apparatus as set forth in claim 21 wherein a vacuum source is operatively connected to said pneumatic valve and a regulator is provided between said vacuum source and said pneumatic valve; and
   said microprocessor providing an output signal to said regulator for controlling the actuation of said pneumatic valve and associated piston.

23. Apparatus as set forth in claim 21 wherein a sensor for said gas delivery means is provided to sense the frequency and length of stroke thereof and sends output signals to said microprocessor.

24. Apparatus for controlling inhalation and exhalation of gas to and from the lungs of a patient comprising:
   gas delivery means for delivering gas to a airway of a patient in a pressure stroke and assisting in the removal of gas from the airway in a suction stroke, said gas delivery means including a pneumatically operated piston having a diaphragm mounted on one end thereof for reciprocation with said piston;
   a solenoid operated pneumatic valve operatively connected to said piston;
   a source of compressed air for said pneumatic valve;
   a regulator between said source of compressed air and said pneumatic valve;
   a microprocessor for controlling and providing an output signal to said regulator for controlling the actuation of said pneumatic valve and associated piston; and a sensor for said gas delivery means to sense the frequency of the operating cycle, the length of the stroke, and the relative time period of the pressure and suction strokes in an operating cycle, said sensor providing output signals to said microprocessor representing the sensed measurements.

25. Apparatus as set forth in claim 24 wherein a vacuum source is operatively connected to said pneumatic valve and a regulator is provided between said vacuum source and said pneumatic valve; and said microprocessor provides an output signal to said regulator for controlling the actuation of said pneumatic valve and associated piston.

26. Apparatus as set forth in claim 25 wherein a pressure transducer is provided adjacent each regulator for sensing the fluid pressure threat, and an output signal is sent by each pressure transducer to said microprocessor representing the positive fluid pressure and negative fluid pressure exerted against said pneumatic valve.

27. Apparatus for controlling inhalation and exhalation of gas to and from the lungs of a patient comprising:

gas delivery means for delivering gas to an airway of a patient in a pressure stroke and assisting in the removal of gas from the airway in a suction stroke, said gas delivery means including a pneumatically operated piston having a diaphragm mounted on one end thereof for reciprocation with said piston;

a solenoid operated pneumatic valve operatively connected to said piston;

a source of compressed air for said pneumatic valve;

a regulator between said source of compressed air and said pneumatic valve;

a microprocessor for controlling and providing an output signal to said regulator for controlling the actuation of said pneumatic valve and associated piston;

a sensor for said gas delivery means to sense the frequency of the operating cycle, the length of the stroke, and the relative time period of the pressure and suction strokes in an operating cycle, said sensor providing output signals to said microprocessor representing the sensed measurements;

a vacuum source operatively connected to said pneumatic valve; and a regulator between said vacuum source and said pneumatic valve;

a pressure transducer for each regulator for sensing the fluid pressure thereat and sending an output signal to said microprocessor representing the positive fluid pressure and negative fluid pressure exerted against said pneumatic valve; and an operator keyboard and associated display operatively connected to said microprocessor for providing desired input information to said microprocessor and for visually displaying desired information on said display.

28. Apparatus for controlling inhalation and exhalation of gas to and from an airway of a patient comprising:

a gas chamber and a gas delivery line extending from the gas chamber to the airway of the patient;

an oscillating member supported in said gas chamber for movement in a pressure stroke in one direction for providing gas to the airway and a suction stroke in an opposite direction for exerting a suction to aid in exhalation of gas from the airway;

a piston and cylinder combination connected to said oscillating member for moving said oscillating member at a desired frequency and length of stroke, said combination including a piston chamber and piston mounted therein for reciprocal movement;

pneumatically operated means operatively connected to said combination for selectively providing air to said piston chamber for driving said piston; and a microprocessor operatively connected to said pneumatically operated means for controlling the volume, frequency and waveform of the gas.

29. A system as set forth in claim 28 wherein said pneumatically operated means includes a solenoid operated pneumatic valve connected to said piston and cylinder combination and a source of compressed air for said pneumatic valve, and said microprocessor provides an output signal for actuation of said pneumatic valve.

30. A system as set forth in claim 29 wherein a regulator is provided between said source of compressed air and said pneumatic valve, and said microprocessor provides an output signal to said regulator for controlling the actuation of said pneumatic valve.

31. A system as set forth in claim 29 wherein said solenoid operated pneumatic valve includes a plurality of redundant solenoid operated pneumatic valves operatively connected to said piston and cylinder combination and being operative only in the event of malfunctioning of the pneumatically operated pneumatic valve.

32. A system as set forth in claim 28 wherein said pneumatically operated means includes a solenoid operated pneumatic valve connected to said piston and cylinder combination;

a source of compressed air for said pneumatic valve utilized in the pressure stroke of the oscillating member;

a vacuum source for said pneumatic valve utilized in the suction stroke of the oscillating member;

a regulator between said source of compressed air and said pneumatic valve;

a regulator between said vacuum source and said pneumatic valve; and said microprocessor providing output signals to said regulator for controlling the actuation of said pneumatic valve and said oscillating member.

33. A system as set forth in claim 32 wherein a pressure transducer is provided for each regulator for sensing the fluid pressure thereat, and an output signal is sent by each pressure transducer to said microprocessor representing the positive fluid pressure and negative fluid pressure exerted against said pneumatic valve.

34. A system as set forth in claim 28 wherein said oscillating member comprises a diaphragm mounted within said gas chamber and exposed to the airway of the patient; and said oscillating member including a disconnect mechanism for removal and replacement.

35. A system as set forth in claim 28 wherein an oxygen source is in fluid communication with the gas delivery line to said airway, and said microprocessor controls the amount of oxygen supplied to the airway from the oxygen source.

36. A system as set forth in claim 28 wherein a source of air and a source of oxygen are in fluid communication with the gas delivery line to said airway, and said microprocessor controls the gas mixture of oxygen and air supplied to the airway.

37. A system as set forth in claim 36 wherein means are provided to moisten said gas mixture supplied to the airway, and said microprocessor controls the amount of moisture supplied to the gas mixture.

38. A system as set forth in claim 36 wherein means are provided to heat said gas mixture supplied to said airway to a predetermined temperature, and said microprocessor controls the predetermined temperature to which said gas mixture is heated.

39. A system as set forth in claim 28 wherein means are provided to vary the time period of the pressure stroke in an operating cycle in relation to the time period for the suction stroke in an operating cycle.

40. A system as set forth in claim 39 wherein the time period for the pressure stroke in an operating cycle is substantially greater than the time period of said suction stroke thereby to assist in the rapid delivery of a predetermined medication to said airway.

41. A system as set forth in claim 39 wherein the time period for the suction stroke of an operating cycle is substantially greater than the time period for said pressure stroke thereby to assist in a rapid removal of fluids from the airway.

42. A system as set forth in claim 28 wherein an anesthesia gas source is provided in fluid communication with said air delivery line to the airway for delivery to the patient.

* * * * *